United States Patent
Yu et al.

(10) Patent No.: US 9,392,936 B1
(45) Date of Patent: Jul. 19, 2016

(54) SYSTEMS AND METHODS FOR DUAL VITREOUS AND RETINA IMAGING

(71) Applicant: NOVARTIS AG, Basel (CH)

(72) Inventors: Lingfeng Yu, Rancho Santa Margarita, CA (US); Hugang Ren, Cypress, CA (US)

(73) Assignee: Novartis AG (CH)

( * ) Notice: Subject to any disclaimer, the term of this patent is extended or adjusted under 35 U.S.C. 154(b) by 0 days.

(21) Appl. No.: 14/623,317

(22) Filed: Feb. 16, 2015

(51) Int. Cl.
*A61B 3/14* (2006.01)
*A61B 3/00* (2006.01)
*A61B 3/10* (2006.01)
*A61B 3/12* (2006.01)

(52) U.S. Cl.
CPC .............. *A61B 3/0025* (2013.01); *A61B 3/0058* (2013.01); *A61B 3/102* (2013.01); *A61B 3/12* (2013.01); *A61B 3/14* (2013.01)

(58) Field of Classification Search
USPC .................................................. 351/206, 246
See application file for complete search history.

(56) References Cited

PUBLICATIONS

Sebag, J., "Imaging vitreous", Eye, 16.4 (2002): 429-439, 2002.
Silverman et al., Pulse-encoded ultrasound imaging of the vitreous with an annular array, Ophthalmic Surgery, Lasers & Imaging, 43.1(2012): 82, 2012.
Liu et al., "Enhanced Vitreal Imaging of the Vitreoretinal Interface in Normal Eyes Using Swept-Source OCT", ARVO 2013, Program No. 3167, 3 pages. 2013.
Jonathan J. Liu, et al; "Enhanced Vitreous Imaging in Healthy Eyes Using Swept Source Optical Coherence Tomography"; PLOS ONE (www.plosone.org); vol. 9; Issue 7; Jul. 18, 2014; pp. 1-10.
Richard F. Spaide; "Visualization of the Posterior Vitreous With Dynamic Focusing and Windowed Averaging Swept Source Optical Coherence Tomography"; American Journal of Ophthalmology; vol. 158; No. 6; Dec. 1, 2014; pp. 1267-1274; Elsevier Inc.; ISSN: 0002-9394.
Giulio Barteselli, et al; "Combined Depth Imaging Technique on Spectral-Domain Optical Coherence Tomography"; American Journal of Ophthalmology; vol. 155; No. 4; Dec. 17, 2012; pp. 727-732. e1; Elsevier Inc., Amsterdam, NL; ISSN: 0002-9394.

*Primary Examiner* — Jack Dinh

(57) ABSTRACT

A system and method for using optical coherence tomography (OCT) to image both the vitreous and the retina in the eye. The image of both tissues may be created sequentially, simultaneously, or near-simultaneously from at least one OCT image.

29 Claims, 4 Drawing Sheets

SYSTEMS AND METHODS FOR DUAL VITREOUS AND RETINA IMAGING

BACKGROUND

1. Field of the Disclosure

The present disclosure relates to systems and methods for using optical coherence tomography (OCT) to image both the vitreous and the retina in the eye. The image of both tissues may be created sequentially, simultaneously or near-simultaneously from at least one OCT image.

2. Background of the Invention

Vitreous body is a transparent gel-like structure in the posterior of the human eye. It provides certain physiological functions to protect the normal human vision, including enabling a metabolic conduit for the lens and removing cells and large macromolecules from the vitreous cavity to maintain its transparency. However, due to aging or pathological processes, disruptions of the gel structure of the vitreous can cause a number of blinding conditions, such as rhegmatogenous retinal detachment, diabetic retinopathy and macular hole. Therefore, visualization of the transparent vitreous and monitoring its changes can be of great interest to the early clinical diagnosis of these pathologies.

For many vitreoretinal diseases, surgical treatment is the only option. During the vitreoretinal surgery, complete and safe vitrectomy is one of the key steps to achieve optimum outcomes. As a result, detection of the residual vitreous and visualizing the vitreous retina interactions during vitrectomy can substantially improve the outcome of current vitreoretinal surgeries.

Due to the transparent nature of the vitreous, direct optical imaging is challenging. Ultrasonography has been used to image the vitreous. However, the resolution and contrast is low and it requires coupling gel, rendering it unsuitable for surgical applications. Optical coherence tomography (OCT) is a high resolution, non-contact and highly sensitive imaging modality which has become the standard in diagnostic ophthalmology. It has been demonstrated that OCT can image the vitreoretinal interface once the vitreous is detached from retina. However, due to the extremely low back scattering, the vitreous body is difficult to image.

Recently, a research group at MIT proposed a technique named enhanced vitreal imaging by adjusting the threshold and contrast of the OCT image to enable visualization of vitreous. However, in the MIT proposed technique the retina image below the vitreous is completely saturated rendering the image overall less useful in surgery.

SUMMARY

A way to image both the vitreous and the retina with OCT is needed.

In one embodiment, the invention relates to a method of receiving as an input OCT data for an eye, segmenting the OCT data, determining the boundary in the OCT data between the retina and vitreous region, processing the OCT data for the retina based on retina characteristics, processing the OCT data for the vitreous based on vitreous characteristics, enhancing the OCT data for the retina based on retina characteristics, enhancing the OCT data for the vitreous based on vitreous characteristics, and fusing the OCT data for the retina with the OCT data for the vitreous.

In another embodiment, the invention relates to a machine readable storage medium, comprising computer-executable instructions carried on the computer readable medium, the instructions readable by a processor, the instructions, when read and executed, for causing the processor to determine the boundary in OCT data between the retina and vitreous region, process the OCT data for the retina based on retina characteristics, process the OCT data for the vitreous based on vitreous characteristics, enhance the OCT data for the retina based on retina characteristics, enhance the OCT data for the vitreous based on vitreous characteristics, and fuse the OCT data for the retina with the OCT data for the vitreous.

In another embodiment, the invention relates to an OCT system containing an OCT source coupled via an OCT transmission medium to a beam splitter coupled via one OCT path to a reference arm; and via a second OCT transmission medium to an OCT focusing element. The OCT system also contains a detector coupled via an OCT transmission medium to the beam splitter. The detector receives an OCT beam containing a component from the reference arm and a component from the OCT focusing element. The OCT system additionally contains a computer electrically or wirelessly coupled to the detector and the actuator. The computer includes a machine readable storage medium, comprising computer-executable instructions carried on the computer readable medium, the instructions readable by a processor, the instructions, when read and executed, for causing the processor to determine the boundary in OCT data between the retina and vitreous region, process the OCT data for the retina based on retina characteristics, process the OCT data for the vitreous based on vitreous characteristics, enhance the OCT data for the retina based on retina characteristics, enhance the OCT data for the vitreous based on vitreous characteristics, and fuse the OCT data for the retina with the OCT data for the vitreous.

BRIEF DESCRIPTION OF THE DRAWINGS

For a more complete understanding of the present invention and its features and advantages, reference is now made to the following description, taken in conjunction with the accompanying drawings, which are not drawn to scale, and in which.

DESCRIPTION OF PARTICULAR EMBODIMENT(S)

Figure 1:
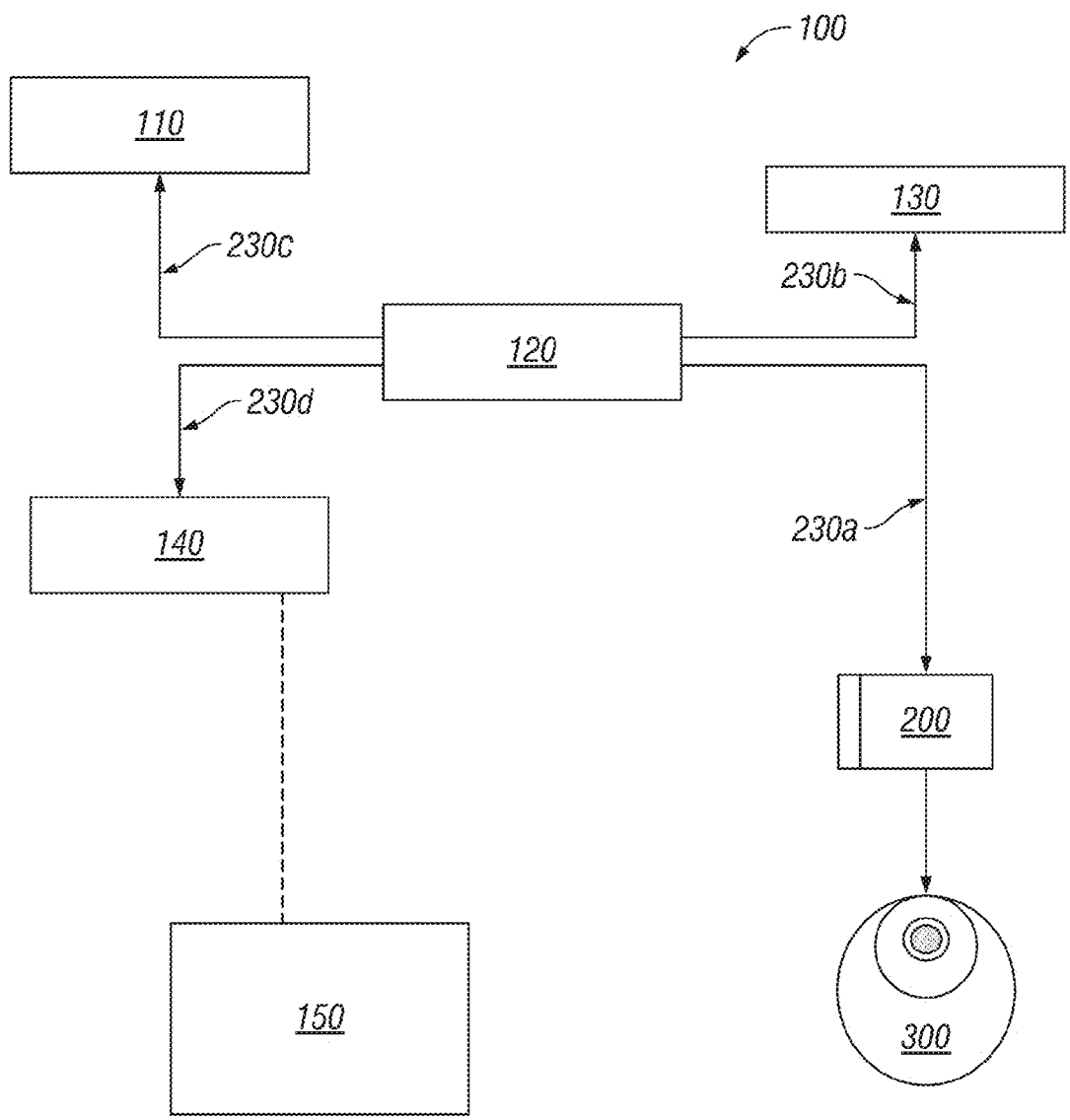
FIG. 1 is an embodiment of an OCT system with sequential, simultaneous or near-simultaneous vitreous and retina imaging.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a reference numeral followed by a letter refers to a specific instance of an element and the numeral only form of the reference numeral refers to the collective element. Thus, for example, device '12a' refers to an instance of a device class, which may be referred to collectively as devices '12' and any one of which may be referred to generically as a device '12'.

Optical coherence tomography (OCT) is an interferometric analysis technique for structural examination of a sample material, such as a tissue that is at least partially reflective to light. It can also be used for functional examination of a sample material, such as the motion and velocity of the sample material or blood flow of the tissue. In OCT, light in the form on an OCT beam is used to measure distances and depth profiles based on optical interference that arises between a reference beam and a sample beam that interacts with the sample material, such as a biological tissue. In some embodiments, the OCT beam may be supplied in pulses, sweeping wavelengths, or a broad band light.

Referring now to the drawings, FIG. 1 is an OCT system 100 with sequential, simultaneous, or near-simultaneous vitreous and retina imaging.

In one embodiment, OCT system 100 may be used during surgery. OCT system 100 may include a heads-up display (not shown) or other display device, such as a two-dimensional image display, a monitor, a TV, or a projector with a screen. OCT system 100 may display a three-dimensional view of the image or a two-dimensional view of the image. In surgery, sequential, simultaneous, or near-simultaneous imaging may occur with a sufficiently short time span to present the surgeon with a combined vitreous-retina image in sufficient time to use the image to modify the surgery while it is occurring. For instance, the image may be presented with no more than one second delay, or no more than half a second delay.

OCT system 100 additionally includes OCT source 110, which produces an OCT beam (not shown) that travels through OCT transmission medium 230c to beam splitter 120 where it is split so that a portion of the beam travels through OCT transmission medium 230b to reference arm 130 and a portion of the beam travels through OCT transmission medium 230a to a beam scanning unit 200. After hitting reference arm 130 or tissue 300, the OCT beams travel back through OCT transmission mediums 230b and 230a, respectively, to beam splitter 120, where they are directed via OCT transmission medium 230d to detector 140. Detector 140 sends a signal to computer 150.

In some embodiments, OCT transmission medium 230 is an optical fiber.

In the embodiment shown in FIG. 1, reference arm 130 is located close to tissue 300 in terms of optical delay and is in a pre-determined position that is an acceptable distance from the OCT source 110. The OCT beam from tissue 300 traveling back through probe 200 to detector 140, interferes with the OCT beam from reference arm 130 and generates an interference pattern.

In one embodiment, reference arm 130 includes a mirror to reflect the OCT beam.

In an embodiment (not expressly shown), a focusing element, which may include a beam scanning element that delivers the OCT beam into different locations may be included.

In one embodiment, detector 140 is a spectrometer. In another embodiment, detector 140 includes a photodiode or similar device that generates an electrical signal indicative of incident light interference signal at detector 140.

Detector 140 may output an electrical signal to computer 150. In such an embodiment, computer 150 may include circuitry for signal conditioning, demodulation, digitization, and digital signal processing. In another embodiment, detector 140 outputs a wireless signal to computer 150.

In one embodiment, computer 150 additionally includes memory media, which store instructions (i.e., executable code) that are executable by the processor having access to the memory media.

In one embodiment, computer 150 includes an image segmentation module, image processing module 202, image enhancing module, and image fusing module. These modules may be implemented as separate software or hardware modules, or combined into a single module. In another embodiment, computer 150 provides OCT image data to a remotely located computer (not shown) which includes an image segmentation module, imaging processing module 202, image enhancing module, and image fusing module.

For the purposes of this disclosure, the memory media may include non-transitory computer-readable media that stores data and instructions for at least a period of time. The memory media may comprise persistent and volatile media, fixed and removable media, and magnetic and semiconductor media. The memory media may include, without limitation, storage media such as a direct access storage device (e.g., a hard disk drive or floppy disk), a sequential access storage device (e.g., a tape disk drive), compact disk (CD), random access memory (RAM), read-only memory (ROM), CD-ROM, digital versatile disc (DVD), electrically erasable programmable read-only memory (EEPROM), flash memory, non-transitory media, and various combinations of the foregoing.

Figure 2:
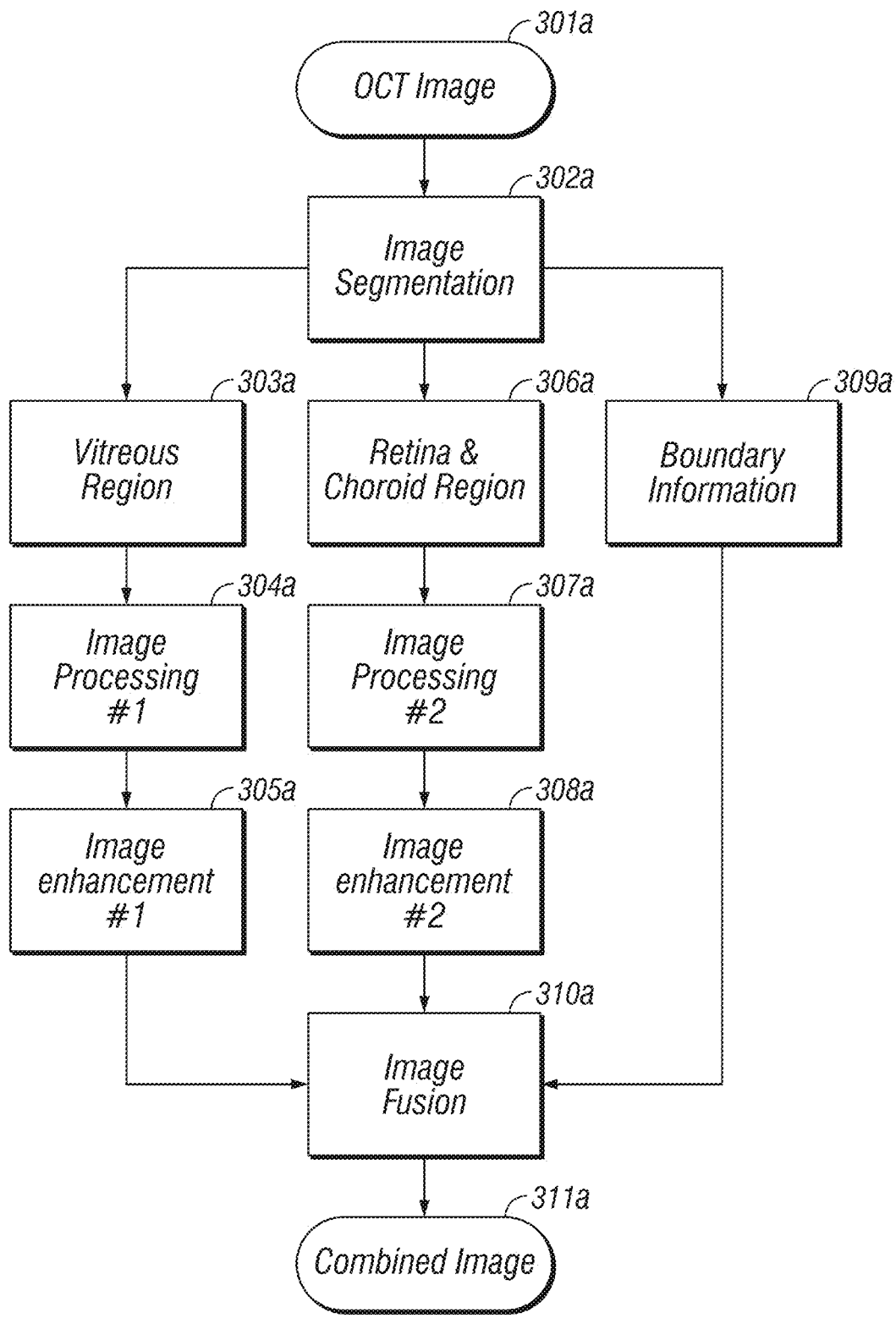
FIG. 2 is flow chart for sequential, simultaneous or near-simultaneous vitreous and retina imaging with OCT using a single image as input.

FIG. 2 is flow chart for sequential, simultaneous, or near-simultaneous vitreous and retina imaging with OCT, such as OCT system 100.

An OCT image is input 301a into the system as part of an OCT scan or from an external input such as the cloud.

Image segmentation 302a is then performed. Image segmentation is the process of partitioning a digital image into multiple segments (sets of pixels). The goal of segmentation is to simplify or change the representation of an image into something that is more meaningful and easier to analyze.

Then OCT image is divided into two separated regions: vitreous region 303a and retina and choroid region 306a. Image processing (304a, 307a) is performed corresponding to the properties of each region. The image contrast, brightness, or dynamic range of each region may be optimized to enhance the structural/functional features and characteristics within the region by image enhancement (305a, 308a).

The vitreoretinal boundary information 309a is identified based on the image segmentation 302a as well. This step 309a may be done before image processing (304a, 307a) and image enhancement (305a, 308a) (310a).

The processed images from the vitreous region and the retina & choroid region are fused or selectively merged together (310a) based on the vitreoretinal boundary information, and a combined image with high dynamic range is obtained, from which both vitreous and retina may be shown on a single image 311a.

Image processing (304a, 307a) may include processing designed to image the retina and processing, designed to image the vitreous. The entire OCT image may be subjected to both types of processing or only segments identified as retina segments may be subject to processing designed to image the retina and any segments identified as vitreous may be subjected to processing designed to image vitreous.

Figure 3:
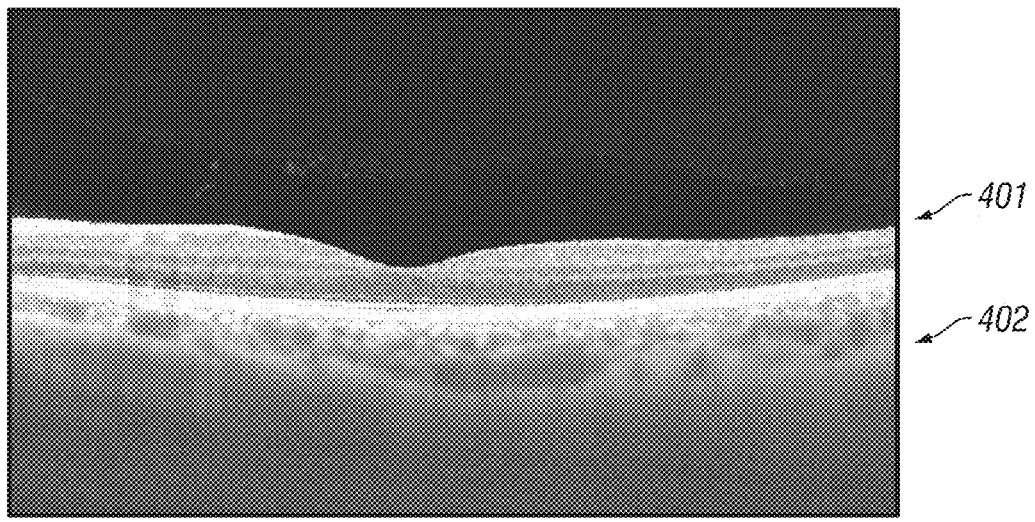
FIG. 3 is a conventional OCT image.
Figure 4:
FIG. 4 is an OCT image created from sequential, simultaneous or near-simultaneous vitreous and retina imaging.

FIG. 3 is a conventional OCT image. In a conventional OCT image, the vitreous region (401) image has relatively weaker OCT signal and the retina and choroid region (402) has adequate OCT signal strength. FIG. 4 is an OCT image created from simultaneous vitreous and retina imaging experiment. The OCT signals of both the vitreous region (401) and the retina and choroid region (402) in FIG. 4 are optimized for better visualization.

Figure 5:
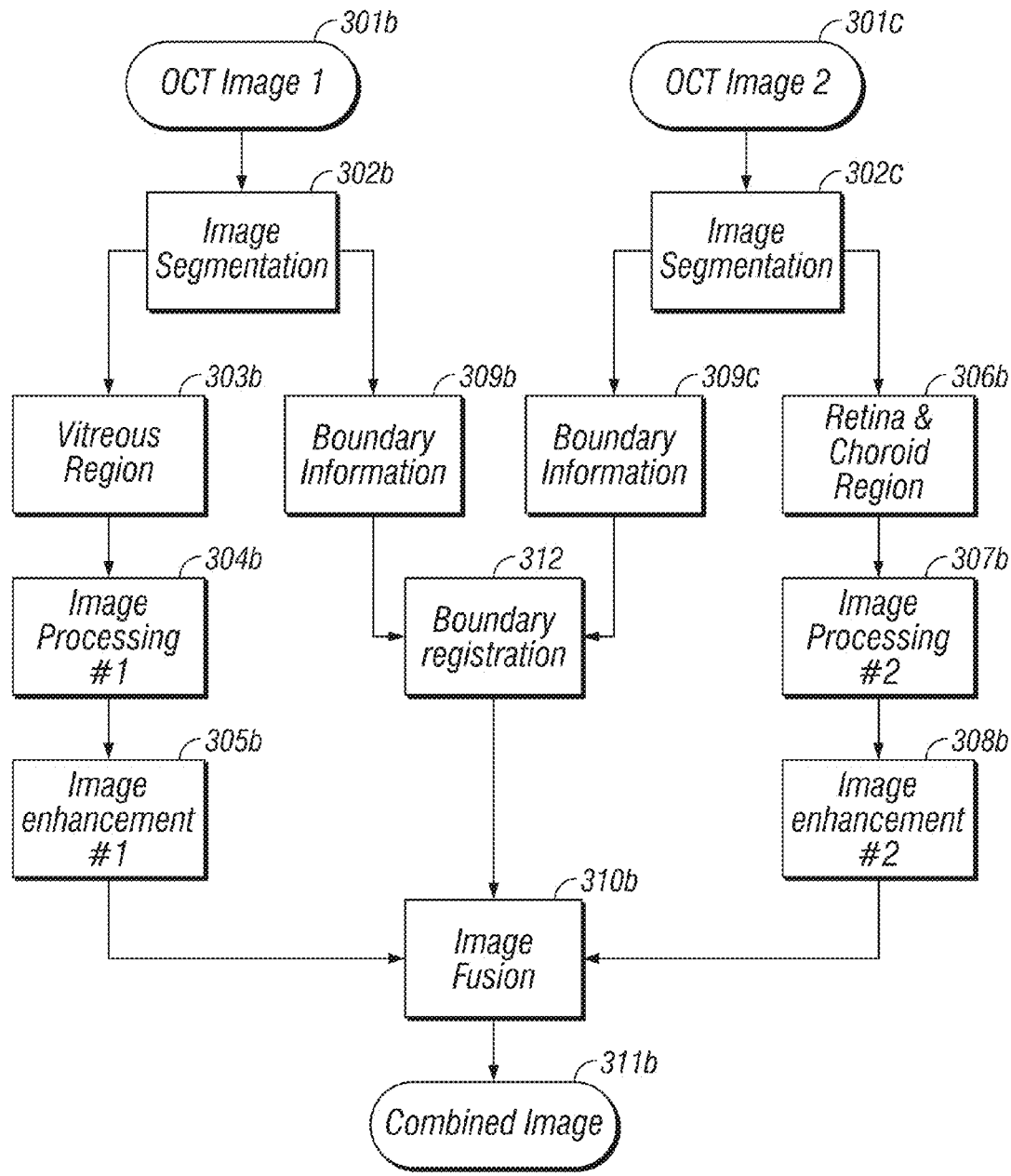
FIG. 5 is a flow chart for sequential, simultaneous or near-simultaneous vitreous and retina imaging with OCT using two images as input.

FIG. 5 is flow chart for sequential, simultaneous, or near-simultaneous vitreous and retina imaging with OCT, such as OCT system 100.

A first OCT image is input 301b into the system as part of an OCT scan or from an external input such as the cloud. A second OCT image is also input 301c into the system as part of an OCT scan or from an external input such as the cloud. The first and second OCT images may be acquired sequentially, simultaneously, or near-simultaneously and from one or two OCT systems such as OCT system 100, or one or two sets of components, such as beam splitter 120 or OCT beam. The first and second OCT images are from the same location in the eye.

Image segmentation 302b and 302c is then performed on both images. Image segmentation is the process of partitioning a digital image into multiple segments (sets of pixels). The goal of segmentation is to simplify or change the representation of an image into something that is more meaningful and easier to analyze. In this example, image 301b is segmented to produce vitreous and boundary information, while image 301c is segmented to produce retina and choroid and boundary information.

Then first OCT image 301b is used to produce vitreous region 303b and the second OCT image 301c is used to produce retina and choroid region 306b. Image processing (304b, 307b) is performed corresponding to the properties of each region. The image contrast, brightness, or dynamic range of each region may be optimized to enhance the structural/functional features and characteristics within the region by image enhancement (305b, 308b).

The vitreoretinal boundary information 309b and 309c from first and second OCT images, 301b and 302c, respectively is identified based on the image segmentation 302b and 302c as well. This step 309b and 309c may be done before image processing (304b, 307b) and image enhancement (305b, 308b).

When two OCT images 301b and 301c are used, then an additional boundary registration step 312 occurs during which the boundary information identified in 309b and 309c from both images is aligned.

The processed images from the vitreous region and the retina & choroid region are fused or selectively merged together (310b) based on the vitreoretinal boundary information, and a combined image with high dynamic range is obtained, from which both vitreous and retina may be shown on a single image 311b.

Image processing (304b, 307b) may include processing designed to image the retina and processing, designed to image the vitreous. The entire OCT image may be subjected to both types of processing or only segments identified as retina segments may be subject to processing designed to image the retina and any segments identified as vitreous may be subjected to processing designed to image vitreous.

Although FIG. 5 illustrates a method using two OCT images, any number more than two may be used by applying a similar methodology. If more than two images are used (or, alternatively to the embodiment illustrated in FIG. 5, even if only two are used), both retinal and vitreous processing and enhancement may be conducted on more than one image, so long as boundary registration step such as step 312 occurs.

In FIG. 5 and other multi-OCT image methods, all image processing may occur sequentially, simultaneously, or near-simultaneously and all image enhancement may occur sequentially, simultaneously, or near-simultaneously.

For sequential imaging, the vitreous image processing may be processed and enhanced before the retina image is processed or enhanced, or vice versa, the vitreous image may be processed, then the retina image processed, the vitreous image enhanced, then the retina image enhanced, or vice versa, or other variations in when image processing and enhancement or other elements of the methods of FIG. 1 and FIG. 5 or other methods described herein occur step-wise. Particularly with sequential techniques, information gained in one step or element of a sequence may be applied to refine or shorten later steps or elements of the sequence.

The present disclosure also includes methods of performing surgery on the eye, such as a vitrectomy, using a segmented OCT image. For instance, the surgery may use a system described in FIG. 1 and a method described in FIG. 2. During such surgery, the surgeon may obtain an OCT image of the eye and use the image to monitor or modify the surgery while it is occurring. For instance, in the case of a vitrectomy, the surgeon may use the OCT image to locate the vireoretinal boundary, to avoid damage to the retina, and to facilitate complete or near complete removal of the vitreous.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. For instance, many example embodiments herein are depicted and described using an OCT system. It will be apparent to one of ordinary skill in the art that a variety of types processors may be included in the computer 150, such as a DSP, field-programmable gate array (FPGA) or graphics co-processor, may be used in such embodiments with corresponding increases in the complexity of calculations.

What is claimed is:

1. A method for imaging vitreous and retina in an eye comprising:
   receiving as an input optical coherence tomography (OCT) data for an eye;
   determining a vitreoretinal boundary in the OCT data between the retina and vitreous region;
   processing the OCT data for the retina based on retina characteristics;
   processing the OCT data for the vitreous based on vitreous characteristics;
   enhancing the OCT data for the retina based on retina characteristics;
   enhancing the OCT data for the vitreous based on vitreous characteristics; and
   fusing the OCT data for the retina with the OCT data for the vitreous to obtain a combined image of the retina, vitreous, and the vitreoretinal boundary.

2. The method of claim 1, wherein the OCT data is derived from at least two OCT images of the same location in the eye.

3. The method of claim 2, wherein the OCT data derived from one image is used to determine the vitreoretinal boundary and to provide OCT data for the retina, while the OCT data derived from a second image is used to determine the vitreoretinal boundary and to provide OCT data for the vitreous.

4. The method of claim 2, wherein the vitreoretinal boundary is determined for all OCT images and aligned for all OCT images.

5. The method of claim 1, wherein the OCT data for the retina further comprises a first subset of the OCT data.

6. The method of claim 5, wherein the OCT data for the vitreous further comprises a second subset of the OCT data.

7. The method of claim 1, wherein the OCT data for the retina further comprises a first copy of the OCT data.

8. The method of claim 7, wherein the OCT data for the vitreous further comprises a second copy of the OCT data.

9. The method of claim 1, further comprising displaying the fused OCT data on a display.

10. The method of claim 1, further comprising displaying the fused OCT data as at least one of a three-dimensional image, a two-dimensional image, an image on a monitor, an image on a display, an image on a TV, or an image in a projector with a screen.

11. At least one machine readable storage medium, comprising computer-executable instructions carried on the computer readable medium, the instructions readable by a processor, the instructions, when read and executed, for causing the processor to:
   determine the vitreoretinal boundary in optical coherence tomography (OCT) data between the retina and vitreous region;
   process the OCT data for the retina based on retina characteristics;
   process the OCT data for the vitreous based on vitreous characteristics;
   enhance the OCT data for the retina based on retina characteristics;
   enhance the OCT data for the vitreous based on vitreous characteristics; and
   fuse the OCT data for the retina with the OCT data for the vitreous to obtain a combined image of the vitreous, retina, and the vitreoretinal boundary.

12. The machine readable storage medium of claim 11, wherein the OCT data for the retina further comprises a first subset of the OCT data.

13. The machine readable storage medium of claim 12, wherein the OCT data for the vitreous further comprises a second subset of the OCT data.

14. The machine readable storage medium of claim 11, wherein the OCT data for the retina further comprises a first copy of the OCT data.

15. The machine readable storage medium of claim 14, wherein the OCT data for the vitreous further comprises a second copy of the OCT data.

16. The machine readable storage medium of claim 11, wherein the OCT data is derived from at least two OCT images of the same location in the eye.

17. The machine readable storage medium of claim 16, wherein instructions are additionally for causing the processor to use OCT data derived from one image to determine the vitreoretinal boundary and to provide OCT data for the retina, and to use OCT data derived from a second image to determine the vitreoretinal boundary and to provide OCT data for the vitreous.

18. The machine readable storage medium of claim 16, wherein instructions are additionally for causing the processor to determine the vitreoretinal boundary for all OCT images and to align the vitreoretinal boundary for all OCT images.

19. An optical coherence tomography (OCT) system comprising:
   an OCT source coupled via a first OCT transmission medium to;
   a beam splitter coupled via a second OCT transmission medium to;
   a reference arm;
   an OCT focusing element coupled via a third OCT transmission medium to the beam splitter:
   a detector coupled via a fourth OCT transmission medium to the beam splitter, wherein the detector receives an OCT beam containing a component from the reference arm and a component from the OCT focusing element; and
   a computer electrically or wirelessly coupled to the detector,
   wherein the computer includes:
      a processor coupled to a computer readable medium; and
      computer-executable instructions carried on the computer readable medium, the instructions readable by the processor, the instructions, when read and executed, for causing the processor to:
      determine the vitreoretinal boundary in the OCT data between the retina and vitreous region;
      process the OCT data for the retina based on retina characteristics;
      process the OCT data for the vitreous based on vitreous characteristics;
      enhance the OCT data for the retina based on retina characteristics;
      enhance the OCT data for the vitreous based on vitreous characteristics; and
      fuse the OCT data for the retina with the OCT data for the vitreous to obtain a combined image of the retina, vitreous, and the vitreoretinal boundary.

20. The OCT system of claim 19 further comprising a display.

21. The OCT system of claim 19, further comprising: at least one of a three-dimensional image display, a two-dimensional image display, a monitor, a TV, or a projector with a screen.

22. The OCT system of claim 19, wherein the OCT focusing element further comprises a beam scanning element that delivers the OCT beam into different locations.

23. The OCT system of claim 19, wherein the OCT data for the retina further comprises a first subset of the OCT data.

24. The OCT system of claim 23, wherein the OCT data for the vitreous further comprises a second subset of the OCT data.

25. The OCT system of claim 19, wherein the OCT data for the retina further comprises a first copy of the OCT data.

26. The OCT system of claim 25, wherein the OCT data for the vitreous further comprises a second copy of the OCT data.

27. The method of claim 19, wherein the OCT data is derived from at least two OCT images of the same location in the eye.

28. The method of claim 27, wherein the OCT data derived from one image is used to determine the vitreoretinal boundary and to provide OCT data for the retina, while the OCT data derived from a second image is used to determine the vitreoretinal boundary and to provide OCT data for the vitreous.

29. The method of claim 27, wherein the vitreoretinal boundary is determined for all OCT images and aligned for all OCT images.

* * * * *